United States Patent [19]
Aronow

[11] Patent Number: 5,851,178
[45] Date of Patent: *Dec. 22, 1998

[54] INSTRUMENTED LASER DIODE PROBE CONNECTOR

[75] Inventor: Kurt Albert Aronow, Lafayette, Colo.

[73] Assignee: Ohmeda Inc., Liberty Corner, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 458,485

[22] Filed: Jun. 2, 1995

[51] Int. Cl.$^6$ ........................................ A61B 5/14
[52] U.S. Cl. ........................................ 600/323; 600/310
[58] Field of Search ........................ 128/632–634, 128/664–666; 600/310–344

[56] References Cited

U.S. PATENT DOCUMENTS

| | | | |
|---|---|---|---|
| 4,913,150 | 4/1990 | Cheung et al. | 128/633 |
| 5,209,203 | 5/1993 | Swedlow | 128/633 |

*Primary Examiner*—David M. Shay
*Attorney, Agent, or Firm*—Roger M. Rathbun

[57] ABSTRACT

This apparatus places the laser diode light source in the connector affixed to the distal end of the cable, proximate to the patient. The disposable portion of the probe simply consists of the apparatus required to affix the probe to the patient's appendage and the mating portion of the connector that interconnects with the cable. The disposable portion of the probe can be a minimalistic design since all the expensive elements are located in the medical monitoring instrument or the cable connector.

27 Claims, 8 Drawing Sheets

INSTRUMENTED LASER DIODE PROBE CONNECTOR

FIELD OF THE INVENTION

This invention relates to medical monitoring probes and, in particular, to a probe architecture that makes use of laser diodes mounted in the cable connector as the light source, which cable connector interconnects with the disposable or reusable segment of the probe that functions to affix the probe to the patient.

PROBLEM

It is a problem in the field of medical monitoring instruments to manufacture a probe that satisfies a number of diverse and sometimes contradictory requirements. It is important that the probe both be simple to use and conform to a variety of patients who differ in size and shape. The probe must be securely affixable to the patient, such as on a patient's appendage, without requiring complex structures or elements that can irritate the patient. In addition, in order to reduce the risk of infection and contamination, the probe is built to be disposable so that the probe is used one or more times with the patient and then destroyed. The probe must be inexpensive so that it can be disposable after use and yet the patient must be shielded from any potentially dangerous electrical signals or heat produced by the probe. The probe must also reliably and accurately perform the required measurements. The probe, cable and monitoring instrument are all subjected to a hostile environment and must be manufactured to be rugged to survive rough handling and the presence of highly reactive fluids. The probe must therefore maintain the required measurement accuracy, be rugged to withstand the hostile environment, be safe for attachment to the patient and yet be inexpensive since it is a disposable element. To achieve these goals compromises typically are made, although the accuracy of the measurements tends to be of paramount importance.

In the specific field of photoplethysmography, the light beams that are generated by the probe must be of sufficient intensity to illuminate the perfused tissue and also be of constant wavelength, since the light absorption of the monitored analyte varies as a function of wavelength. Light emitting diodes (LEDs) that produce light beams at red and infrared wavelengths are typically used in the probe for this purpose. The production of an intense beam of light must be balanced with the requirement that the probe does not operate at a significantly elevated temperature, which would cause irritation to the patient's skin. A complicating factor is that the light emitting diodes are mounted in the probe module, and are juxtaposed to the patient's skin. The light emitting diodes are therefore subject to significant temperature fluctuations, resulting in changes in wavelength of the light output by the light emitting diodes, which causes a measurable source of error in the measurements that are taken by the monitoring instrument device.

It is preferable in photoplethysmographic systems to use laser diodes, which produce a beam of substantially monochromatic light at or exceeding the light power available from light emitting diodes that are typically used in photoplethysmography. The difficulty with laser diodes is that their cost prevents them from being used in a disposable probe. Placement of the laser diode in the monitoring instrument necessitates the use of one or more fiber optic strands in the cable that interconnects the disposable probe with the monitoring instrument. The cable in a hospital environment typically suffers rough handling and the life of the fiber optic strands in the connector cable can be fairly limited, thereby increasing the effective cost of the disposable probe since the cable must typically be replaced on a fairly frequent basis.

Thus, there presently does not exist a monitoring instrument that can fully satisfy the plurality of diverse requirements in a manner that does not compromise the performance of the monitoring instrument.

SOLUTION

The above-described problems are solved and a technical advance achieved in the field of medical monitoring instruments by the apparatus of the present invention which makes use of a monochromatic light source, such as laser diodes, to produce high intensity substantially monochromatic beams of light. In the preferred embodiment disclosed herein, the monitoring instrument and probe comprise an arterial blood monitoring instrument, such as a pulse oximeter instrument, hemoglobin monitor or total hemoglobin monitor, which noninvasively monitors blood analytes in the patient. The use of monochromatic light improves the accuracy of the measurements and simplifies the calibration process.

This apparatus places the laser diodes in the connector at the distal end of the cable proximate to the disposable portion of the probe to thereby implement an instrumented connectorized laser diode probe cable. Placement of the laser diodes in the connector at the probe eliminates the need for the fiber optic strands in the cable and yet provides the benefits of laser diode light generation over the presently used light emitting diodes. Furthermore, the disposable section of the probe can be a minimalistic design since all the active and expensive elements are located in the cable connector. The disposable section of the probe simply consists of the apparatus required to affix the probe to the patient's appendage and the mating portion of the connector that interconnects with the cable and a photodetector. This probe apparatus therefore overcomes the problems of prior art probes by making use of laser diodes as the light generating elements, wherein the laser diodes are not part of the disposable section of the probe. The disposable section of the probe is simplified to comprise the minimum number of elements to thereby reduce the cost of below that of present light emitting diode based probes.

DETAILED DESCRIPTION

Figure 1:
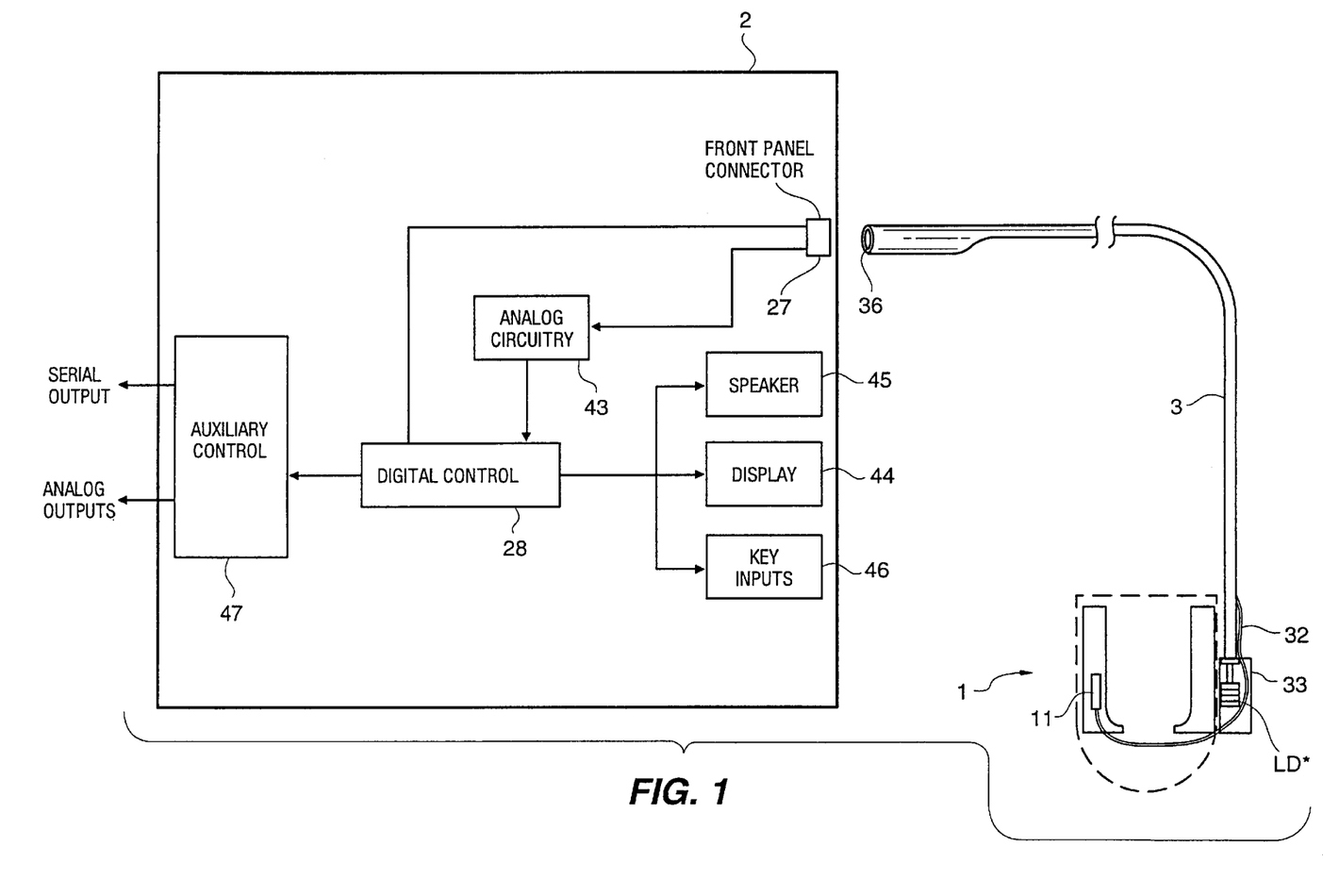
FIG. 1 illustrates the architecture of the probe of the present invention, including a side cutaway view of the probe module and a block diagram of the control elements of the monitor.

Any improvements, however incremental, in the design and manufacturability of a probe in the field of medical monitoring instruments result in significant cost savings. The apparatus of the present invention consists of two segments: an electronics (control) module, typically resident within the monitor, and a probe module that is affixed to a probe attachment site on the patient. FIG. 1 illustrates the probe module in side cutaway view and a block diagram of the elements that comprise the control module. FIGS. 4, 5 and 7–9 illustrate details of the probe module implementation. The apparatus of the present invention represents an architecture in which the configuration of elements are cooperatively operative to solve the problems of existing medical monitoring instrument probes.

Photoplethysmographic Probe Application

A pulse oximeter instrument is frequently used to monitor the condition of a patient in a hospital setting. The pulse oximeter instrument noninvasively measures the oxygen saturation of the arterial blood and produces a human readable display that indicates both the patient's heart rate and the oxygen saturation of the arterial blood. These readings are important to enable the medical staff to determine whether the patient's respiratory system is functioning properly, supplying sufficient oxygen to the blood.

A pulse oximeter instrument operates by use of a probe that illuminates an appendage of the patient (such as a finger, earlobe, or the nasal septum) that is rich in arterial blood and measures the differential absorption of the light by the pulsatile portion of the arterial blood flow to thereby determine oxygen saturation of the arterial blood. The pulse oximeter instrument makes use of a plurality of light-emitting devices, each of which transmits light at a predetermined wavelength, which wavelengths are selected such that at least one is highly absorbed by oxygenated hemoglobin in the arterial blood and at least one is highly absorbed by reduced hemoglobin in the arterial blood. The amount of absorption of the light beams generated by these light emitting devices that are located in the probe is a measure of the relative concentration of the various hemoglobin species contained in the arterial blood. The absorption of the light that illuminates the appendage of the patient includes a constant portion that is a result of skin, bone, steady-state (venous) blood flow and light loss due to various other factors. The pulsatile component of absorption is due to the pulsatile arterial blood flow and is a small fraction of the received signal and is used by the pulse oximeter instrument to perform its measurements. It is also possible to measure additional analytes in the arterial blood, such as additional dyshemoglobins (Met Hb and CO Hb), with one additional wavelength of light for each component. A monochromatic light source is desirable for these additional wavelengths of light to avoid overlap of the "tail ends" of each spectral characteristic.

The measurements are computed by sampling the output of the light detector located in the probe to determine the incremental change in absorption of the various wavelengths of light that are used to illuminate the appendage of the patient. These incremental changes in light absorption are then used to compute the oxygen saturation of the arterial blood as well as the patient's pulse rate. Since the pulsatile component of the signals received by the light detector represent only a small fraction of the incident light, it is important that the incident light be of significant magnitude to result in transmitted signals that have sufficient amplitude to provide accurate readings. In addition, the probe containing the light-emitting devices and the light detector must be placed in intimate contact with the skin of the patient to obtain the most accurate readings. The probe design must therefore be such that it inherently accommodates variations in size and shape of the patient's appendage and also enables the medical staff to simply align the probe to obtain the maximum readings. These stringent requirements are difficult for existing probes to comply with and increase the manufacturing cost of the probes, which may be disposable elements.

Probe Philosophy

Figure 6:
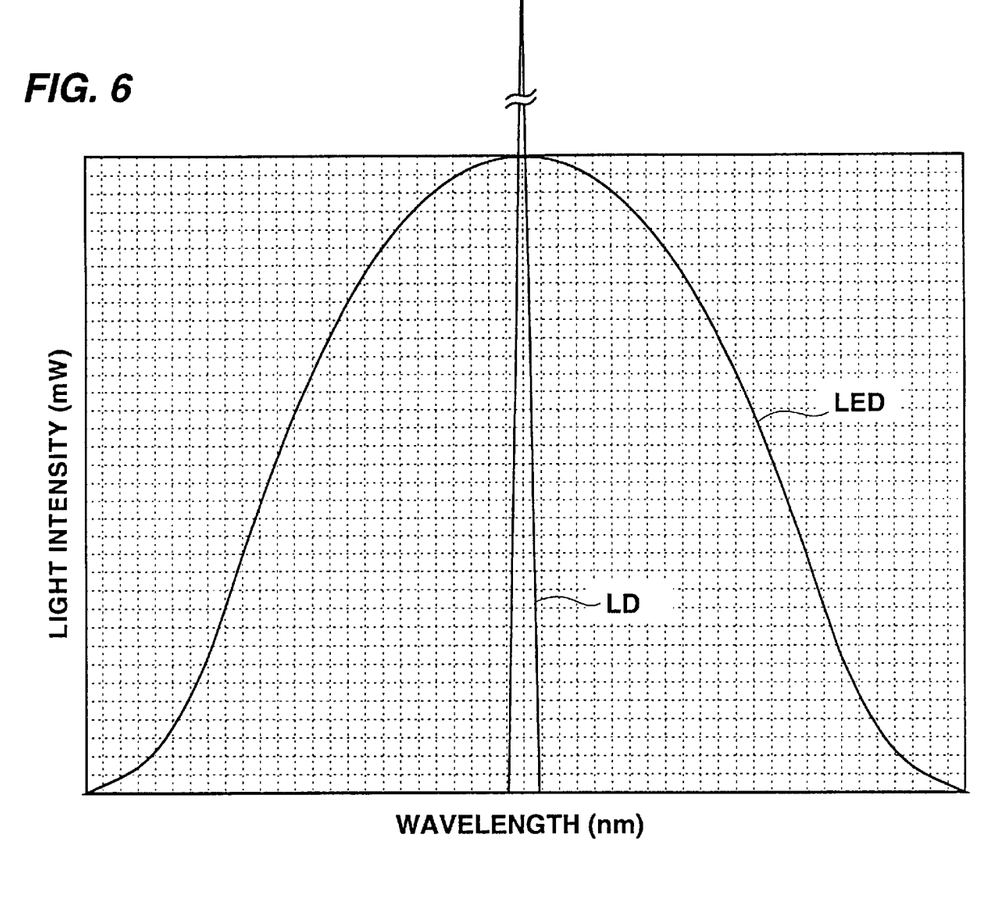
FIG. 6 illustrates a waveform of the comparative light output of laser diodes and light emitting diodes.

The light emitting devices used in the photoplethysmographic (pulse oximeter) instrument application disclosed herein are laser diodes, which produce an intense beam of light that is substantially monochromatic. The selection of laser diodes to generate the light beams that are used to illuminate the perfused tissue of the patient is a result of the preferable output characteristics of the laser diode as compared to the light emitting diode. FIG. 6 illustrates the spectral output of these respective devices, with the laser diode producing a beam of light, whose spectral output (LD) is centered about a selected wavelength, such as 660 nm, and having a bandwidth of as little as 1 nm. The light emitting diode produces a beam of light, whose spectral output (LED) is centered about a selected wavelength, such as 660 nm, and having a bandwidth of 60 nm width or greater. Thus, the laser diode is able to generate a great deal of power over a narrow spectral range when compared to a light emitting diode.

In addition to the extent of the bandwidth, the variations in bandwidth and shape of the spectral output curve among light emitting diodes represent a significant problem. The tail end of the spectral emissions of the light emitting diode can have a measurable effect on the received signal from the perfused tissue. The magnitude and extent of the tail portion of the spectral emissions is more difficult to measure and account for than the signal output at maximum intensity. A complicating factor is that the light emitting diodes are mounted in the probe module, and are juxtaposed to the patient's skin. The light emitting diodes are therefore subject to significant temperature fluctuations and the corresponding changes in wavelength output by the light emitting diodes, which cause a measurable source of error. Finally, another source of error is the "venous prefiltering", wherein the spectral output of the light emitting diodes is unevenly and unpredictably attenuated across the range of generated wavelengths of light by the presence of the venous and non-pulsatile arterial components of the blood. This attenuation of the light is a function of the oxygen saturation of the blood and wavelength, varies from subject to subject, and also is temporal in nature, varying within a given patient. The arterial blood flow is highly variable in the extremities of a patient, where the pulse oximetry readings are taken. The difference in oxygen saturation between arterial and venous components of the blood can be from as little as less than one percent to greater than twenty-five percent. Thus, the greater the spectral bandwidth, the greater this source of error. The light emitting diode and the method of placing it on the patient's appendage to perform readings have inherent sources of error that cannot be accurately quantified or compensated.

Probe Architecture

The apparatus of the present invention consists of two primary segments: a control module 2, typically resident within the monitor, and a probe module 1 that is affixed to a probe attachment site on the patient. These two modules 1, 2 are interconnected by a cable 3 which can be affixedly attached to and an integral part of probe module 1 or can be an element that is connectorized at both ends thereof to enable cable 3 to be disconnected from both probe module 1 and control module 2. In the embodiment disclosed herein, cable 3 is shown as interconnected with probe module 1 via a connector.

Control Module

The control module 2 includes circuitry to receive the return signals produced by the reception of light that passes through the illuminated appendage as well as user interface circuitry. The control module 2 includes analog circuitry 43 that functions to receive and condition the electrical signals produced by the light detector 11 that is contained within the probe module 1, as is well known in the art. These received signals are digitized and transmitted to digital control 28 for processing as is well known in the field to produce the required measurements. The digital control 28 outputs the computed measurements to display 44 for production of a human-readable output. A speaker 45 is typically included to enable digital control 28 to produce audible alarms to alert the user to error or danger conditions. Key inputs 46 are also typically provided to enable the user to input control information to regulate the operation of the instrument. An auxiliary control circuit 47 receives output signals from digital control circuit 28 for transmission in serial and/or analog form to other elements in the medical monitoring instrument.

Cable Connector

The cable connector 82 consists of the light generation apparatus (laser diodes), conductor 32 to connect to the light detector 11 in probe module 1 and optical apparatus that applies the light beams generated by the laser diodes to the patient's appendage. A plurality of laser diodes are noted in FIG. 1, labeled as "LD*". The number of laser diodes LD* is equal to or greater than the number of blood analytes that are to be measured by the instrument. For standard pulse oximetry, the number of laser diodes can be as little as two, one whose light output is at a wavelength of approximately 660 nm and a second whose light output is at a wavelength of approximately 940 nm. In the system disclosed herein, four laser diodes LD* are disclosed. The wavelength of the light beams output by the laser diodes LD* are affected by the operating temperature of the laser diodes LD*. This configuration allows the light generated by the laser diodes LD* in the cable connector 82 to be output therefrom in a cone shaped pattern, whose symmetric axis is substantially perpendicular to the patient's skin, so while the generated light is incident on the patient's skin, the laser diodes LD* are not in intimate contact with the patient's skin.

Probe Cable Connector Implementation Details

Figure 7:
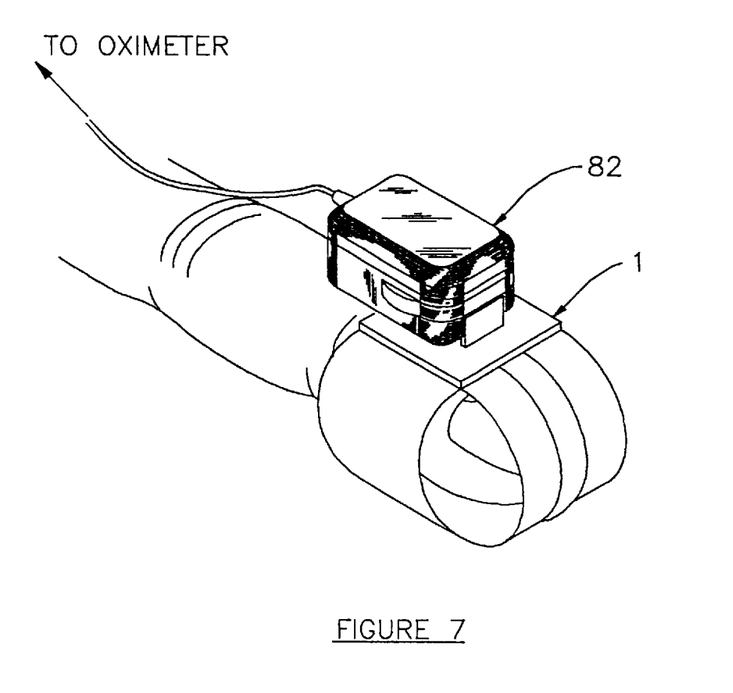
FIGS. 7 and 8 illustrate an alternative implementation of the probe module.
Figure 8:
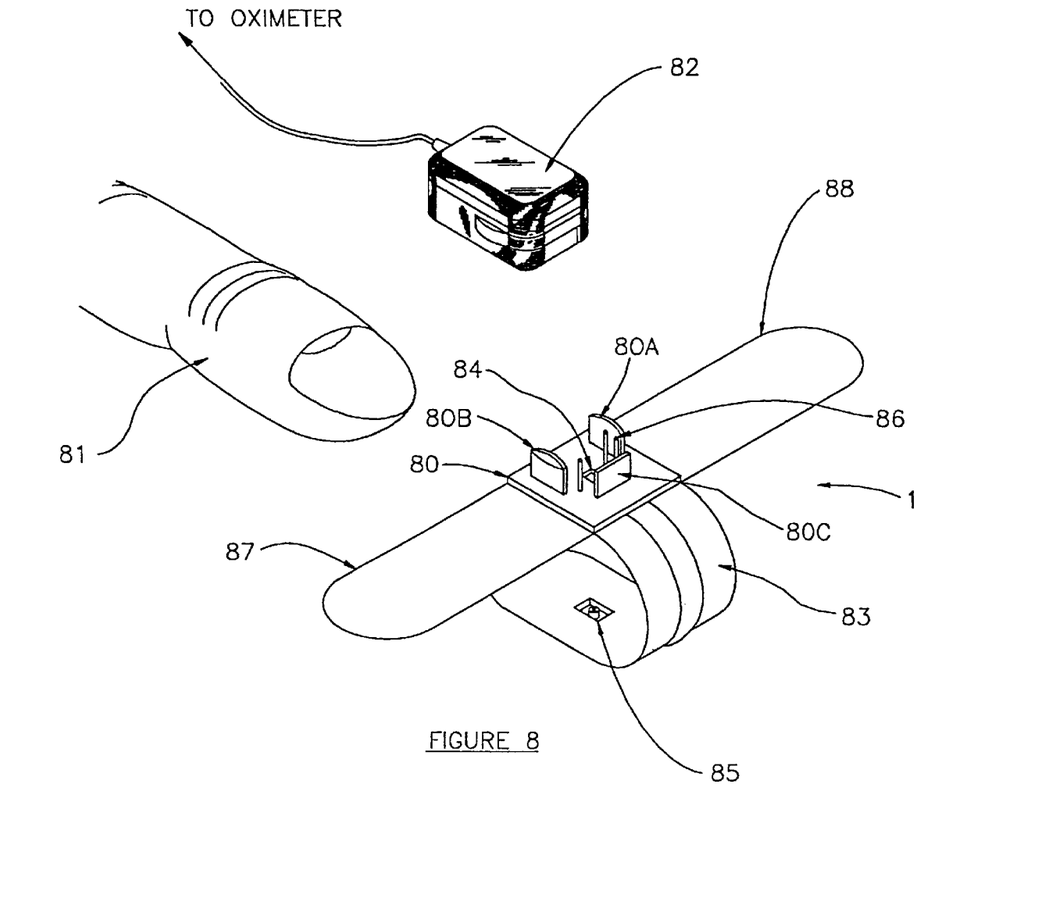

The implementation details of the preferred embodiment of the cable connector 82 of the present invention is disclosed in additional detail in FIGS. 4, 5, 7–9. FIGS. 7 and 8 illustrate the probe 1 and cable connector 82, (which contains the laser diodes) interconnected together (FIG. 7) and separated into the individual parts (FIG. 8). The probe of FIG. 8 comprises a bandage type of implementation, wherein connector segment 80 interconnects light detector 85 and optical port 84 with cable connector 82. A plurality of projections 80A, 80B, 80C serve to align cable connector 82 with pins 86 of connector 80 and securely affix cable connector 82 with connector 80, as described below. Flexible segment 83 wraps around the tip of the patient's finger 81 as shown in FIG. 7 and the probe 1 is securely held in place on the patient's finger by adhesive strips 87, 88 in well known manner.

Figure 4:
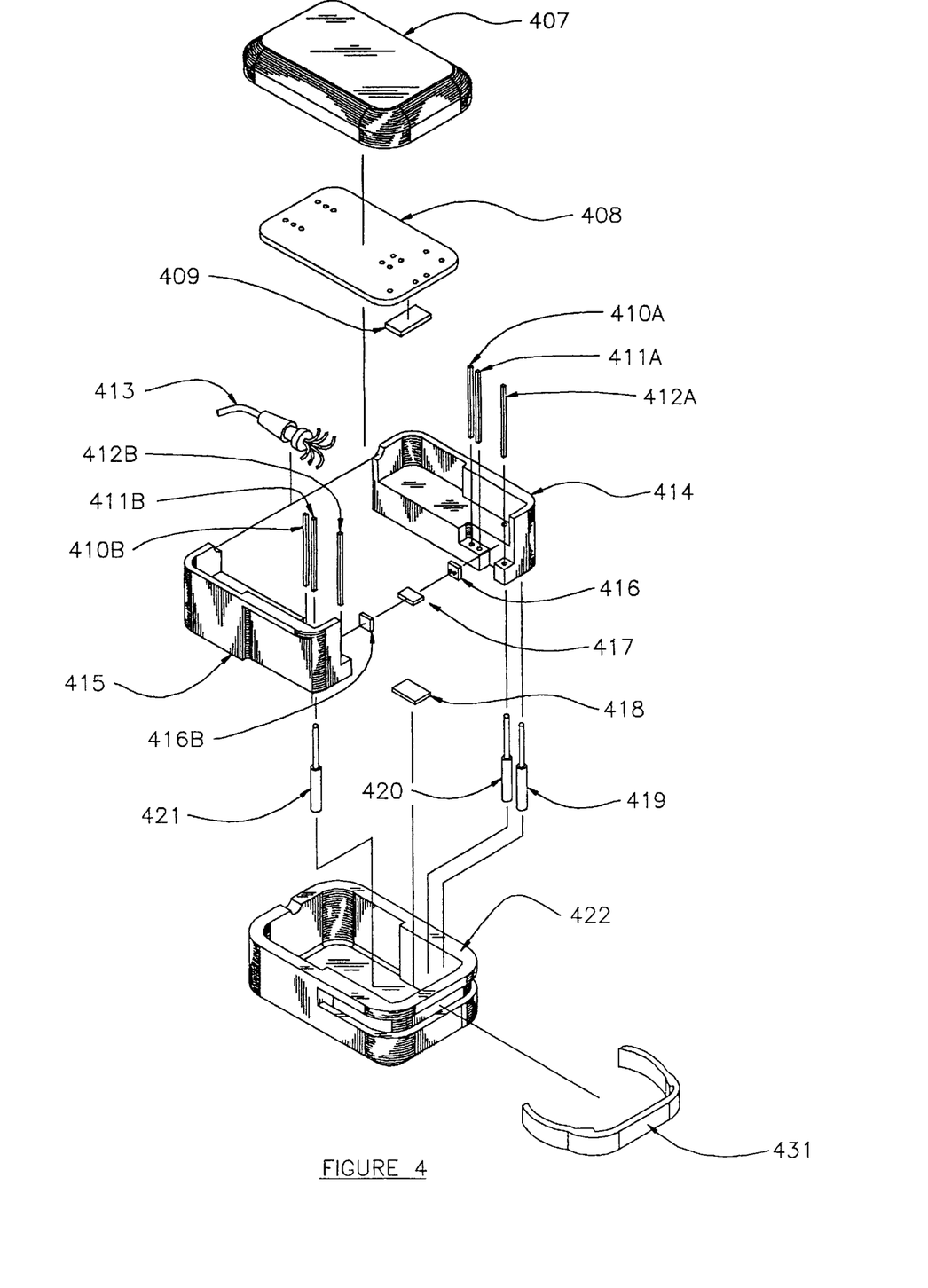
FIGS. 4 and 5 illustrate top isometric and bottom isometric views (exploded) of the cable connector.
Figure 5:
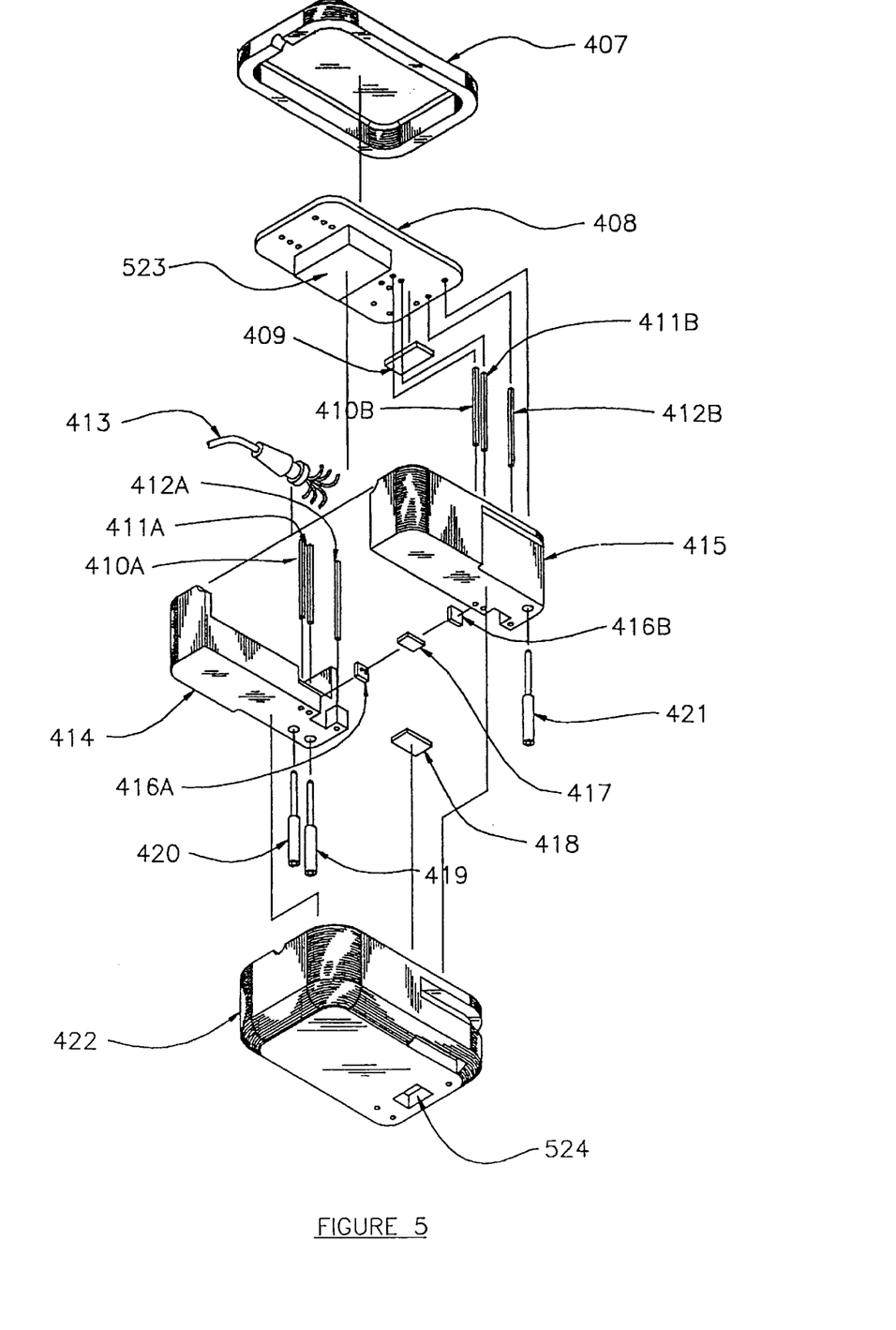

FIGS. 4 and 5 illustrate top isometric and bottom isometric exploded views, respectively, of the cable connector 82. This cable connector 82 comprises a housing 422 that is equipped with cover 407 to enclose and protect the remaining elements from the ambient environment. Included in cable connector 82 is a pair of heat sinks 414, 415 which serve to maintain the plurality of laser diodes 416A, 416B at a moderate operating temperature. The heat sinks 414, 415 seat within housing 422 and may be thermally interconnected via a coating of thermally conductive paste applied to the mating surfaces thereof. Heat sinks 414, 415, when installed in housing 422, provide a shelf on which circuit board 408 rests. The circuit board 408 contains circuit element 523 which provides at least some of the analog and digital circuitry that is used to interface with the laser diodes 416A, 416B and light detector 11. The circuit board 408 may largely obviate the need for the analog circuitry 43 illustrated on FIG. 1. Photodetector 409 is also mounted on circuit board 408 and functions, in conjunction with circuit element 523 to regulate the output of laser diodes 416A, 416B. Cable 3 is terminated on circuit board 408 via strain relief 413, which also provides an environmental seal as it passes through a corresponding opening in housing 422. A plurality of connector sockets 419–421 pass through and are aligned by insulated holes in heat sinks 414, 415 to connect to circuit board 408 and the circuit element 523. The connector sockets 419–421 function as the conductors that interconnect cable connector 82 with corresponding connector pins 86 on probe connector 80. Spring clip 431 functions to secure the cable connector 82 with probe connector 80 when the two elements are physically interconnected as shown in FIG. 7. The projections 80A, 80B fit into mating holes on the bottom of housing 422 and snap fit with spring clip 431 as they pass through these holes. A user can thereby disconnect the cable connector 82 from probe connector 80 by simply applying force to the exposed section of spring clip 431 to deflect projections 80A and 80B a sufficient distance to clear the edges of the holes in the bottom of housing 422.

Figure 9:
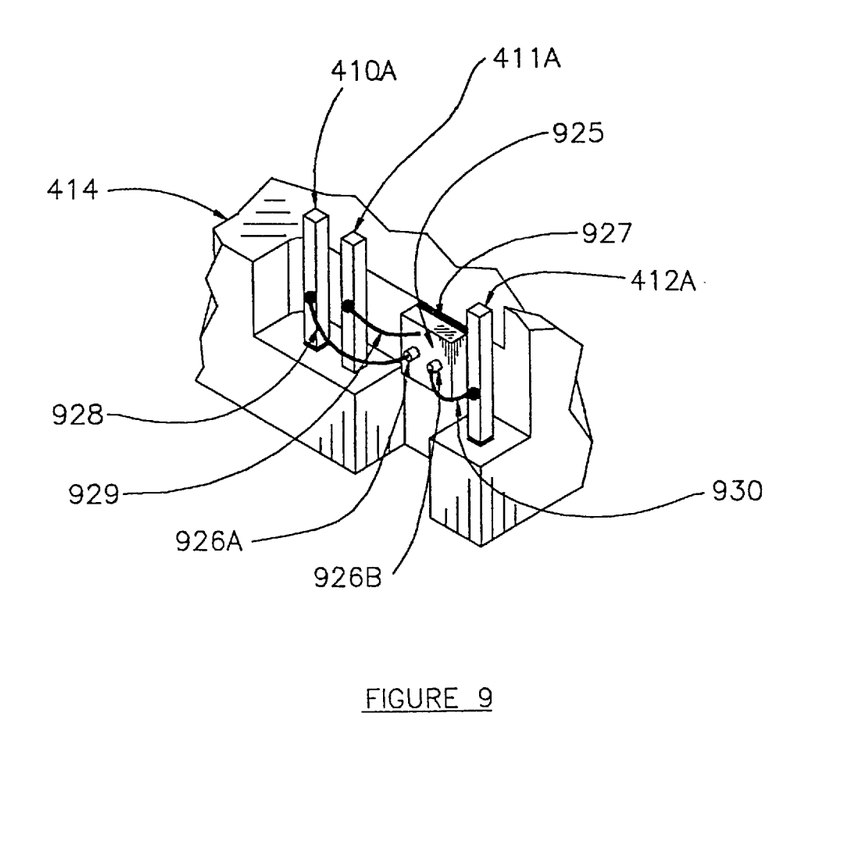
FIG. 9 illustrates a top isometric view of the laser diode wiring assembly.

FIG. 9 illustrates additional details of the laser diode installation in cable connector 82. The four laser diodes are installed in two pairs 416A, 416B, with each pair of laser diodes being mounted via substrate base 925 and thermally conductive bonding agent 927 on a corresponding heat sink 414, 415 for thermal dissipation. Three pins 410A, 411A, 412A are installed in heat sink 414 to provide conductors to which the terminals of laser diodes 926A, 926B are connected. Conductor 411A is electrically connected to heat sink 414 and to laser diodes 926A, 926B via conductor 929. Pins 410A and 412A are electrically insulated from heat sink 414 and function to interconnect the laser diodes 926A, 926B with circuit board 408. Conductors 928, 930 function to connect laser diodes 926A, 926B to pins 410A, 412A. The light output of laser diodes 926A, 926B is carried through window 418 through opening 524 in housing 422. Window 418 may be clear or at least partially diffusing to prevent damage to a user's eye if the user were to look directly into the beam of light generated by the laser diodes 926A, 926B and exiting the cable connector 82. An opaque shade 417 is provided to prevent optical transmission of ambient light from opening 524 to photodiode 409.

Alternative Probe Implementations

Figure 2:
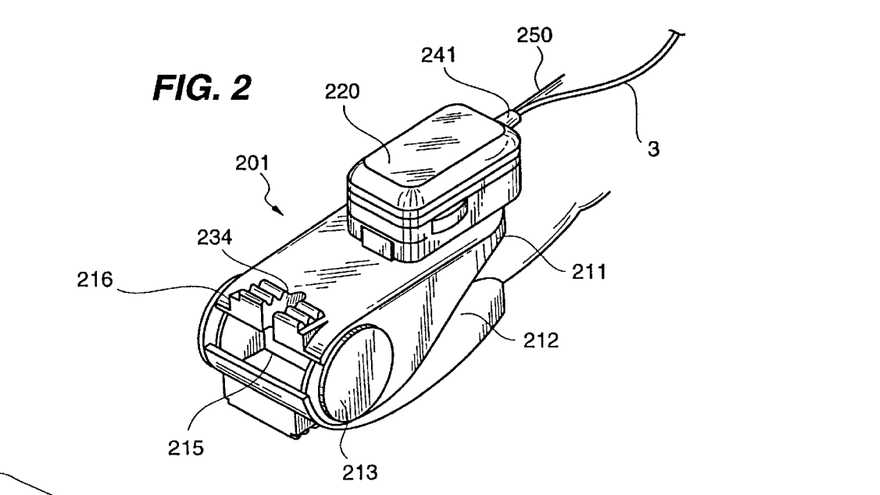
FIGS. 2 and 3 illustrate one implementation of the probe module.
Figure 3:
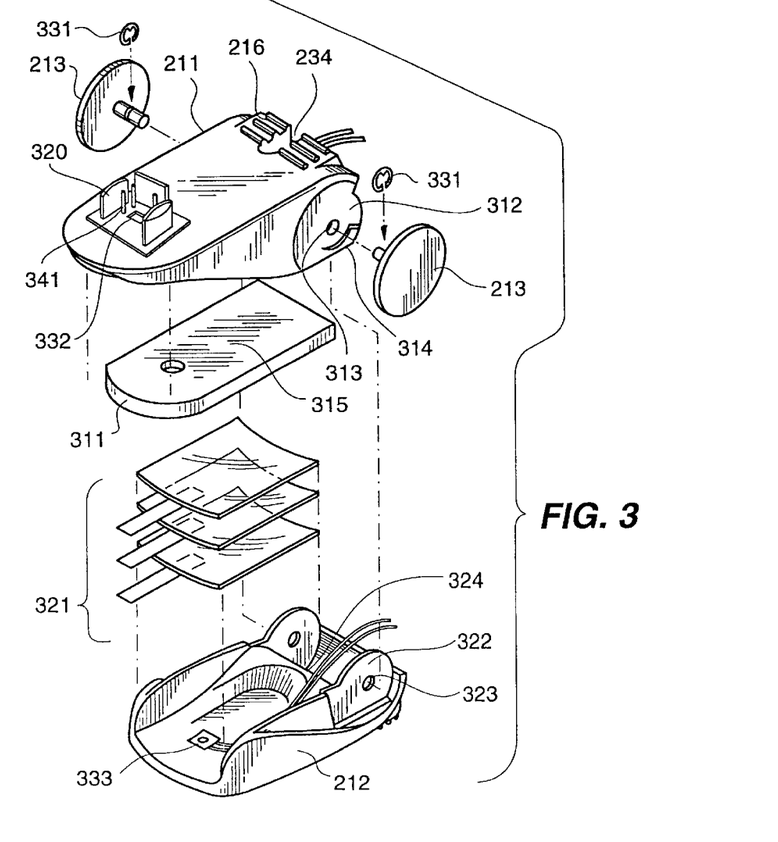

FIGS. 2 and 3 illustrate perspective and exploded views of one implementation of a probe module 1. This configuration is a "clip-tip" or "spring clip" probe that makes use of a spring loaded pair of opposing arms 211, 212 to precisely place the patient's finger in the proper position with respect to the optical port 332 and light detector 333 elements and to place these elements in contact with the patient's skin at the probe attachment site. The spring clip probe 1 consists of a first section 211, which is equipped with a conformable pad 311 attached to the interior surface of first section 211 and having an aperture 315 to permit light to pass from optical port 332 to the patient's finger that is placed in the spring clip probe. Also included in the first section 211 is a connector 320 for interconnecting a cable 3 to the light detector 333 included in the spring clip probe 1 and positioning the optical elements contained in the connector 220 over the optical port 332. The second section 212 of spring clip probe 1 includes light detector 333 and an adhesively coated material 321 that serves to affix the spring clip probe 1 to the patient's finger 250. The first section 211 and the second 212 section are similar in configuration and, when fitted together, function to press the optical port 332 and light detector 333 against a patient's finger 250 that is inserted between the first 211 and second 212 sections. The first 211 and second 212 sections are hingeably attached to each other and include a spring member 314 integral to the first section 211 that functions to bias the first 211 and second 212 sections together in a closed position as illustrated in FIG. 2. First 211 and second 212 sections include mating pieces that, when assembled with a pivot pin 213, function as a hinge. In particular, the first section 211 includes two areas 312, each of which has an aperture 313 formed therein to correspond to a mating aperture 323 in areas 322 on the second section 212. The first 211 and second 212 sections are aligned and interconnected by the insertion of pivot pins 213 in the respective apertures 313, 323 when oriented opposite each other such that the tissue contacting surfaces of the interior surfaces of first and second sections 211, 212 face each other. The integral spring 314 that is part of first section 211 exerts a force against the second section 212 to force the ends of the first and second housing sections 211, 212 apart, which cause the first and second housing sections 211, 212 to rotate with respect to each other around the pivot pins 213, thereby forcing the other ends of the housing together.

The interior surface of the first 211 and second 212 sections include a curved portion to substantially parallel the contours of a typical finger 250 to which the spring clip probe I is connected. The conformable pad 311, and adhesively coated material 321 function to compensate for topological differences between the patient's finger 250 and the curvature of the inside of the two sections 211, 212 of the spring clip probe 1. Thus, when the two sections 211, 212 of the spring clip probe 1 are closed about a patient's finger 250, the conformable pad 311 and adhesively coated material 321 form a surface that substantially maps to the contours of the patient's finger 250. The use of the conformable pad 311 and adhesively coated material 321 and the spring mechanism 314 of the spring clip probe 1 ensures that the optical port 332 and the light detector 333 are placed in close and firm contact with the skin of the patient's finger 250. The close contact of the optical port 332 and the light detectors 333 with the patient's finger 250 is critically important since any ambient light that is received by the light detector 333 interferes with the measurement of the particular characteristics of the arterial blood that are performed by the monitoring equipment.

The interior surface of the second section 212 is also shaped to match the contours of the bottom of a finger 250 such that the interior end 324 of this recess functions as a finger stop which is designed to position the patient's finger 250 inside of the housing section 212 at a predetermined location. The height of the finger stop 324 is designed to permit a fingernail, especially a long fingernail, to pass over the top, but also to prevent the fleshy fingertip from extending beyond a selected point between the two sections 211, 212 of the spring clip probe 1. The light detector 333 is mounted in the bottom of the contoured area of second section 212 in a predetermined location.

In order to prevent the movement of the patient's finger 250 within the spring clip probe 1, the adhesively coated material 321 located in the second section 212 is implemented by means of at least one and preferably a plurality (shown in FIG. 3) of layers of clear conformable material 321 that are adhesively coated on both sides thereof. The conformable pad 311 adhesively affixed to the first section 211 can be manufactured of an opaque material having an aperture (hole) 315 cut therein to allow the optical port 332 affixed to the interior surface of the first section 211 of the spring clip probe 1 to transmit light through the hole 315 in the conformable pad 311 to shine on the patient's finger 250 at a predetermined location, such as near the cuticle of the finger.

The construction of the first section 211 and second section 212 of the spring clip probe 1 is such that, when closed on the patient's finger 250, the first 211 and second 212 sections have surfaces conforming to the patient's finger 250 and close akin to a clam shell. The hingeably connected ends of the first 211 and second 212 sections of the spring clip probe 1 are cut such that in a closed position an aperture 215 is provided between the first 211 and second 212 sections. This aperture 215 is closed when the first 211 and second 212 sections are opened to the full extent, the range of travel being determined by the size of the aperture 215. Therefore, when placed in a fully opened position the pivoting end of the first 211 and second 212 sections encounter each other, restricting the range of motion of the first 211 and second 212 sections.

The light detector 333 is of conventional design typically found in pulse oximeter probes. The plurality of conductors are connected to the light detector 333 and these conductors are terminated in a connector 220 located on the top surface of the first section 211 of the spring clip probe 1. This connector 220 includes a plurality of pins 341 arranged in a predetermined pattern therein, which connector 220 is located at the patient end of the spring clip probe 1 in order to provide the user with sufficient space to grasp the spring clip probe 1 for application to the patient's finger 250.

I claim:

1. Apparatus for illuminating tissue of a subject to measure light absorption of said tissue by a measurement system, comprising:

an interconnector cable wherein said interconnector cable comprises:

a first connector segment having an opening in one side thereof;

at least two laser diode light sources, mounted in said first connector segment, for generating at least two beams of light of different wavelengths for application to said tissue through said opening;

a plurality of electrical conductors electrically interconnected between said at least two laser diode light sources and said measurement system;

a probe wherein said probe comprises:

a second connector segment, removably interconnectable with said first connector segment, for interfacing said interconnector cable with said probe;

wherein said second connector segment includes an optical port for transmitting said at least two beams of light to said tissue wherein said optical port is located substantially adjacent said opening of said first connector segment when said first connector segment is removably interconnected with said second connector segment; and attachment means connected to said second connector segment adapted for removably attaching said probe to said subject.

2. The apparatus of claim 1 wherein said optical port comprises:

an optically transmissive window for transmitting said generated beams of light from said first connector segment through said second connector segment to said tissue, when said first and second connector segments are interconnected.

3. The apparatus of claim 1 wherein said attachment means comprises:

a flexible support structure for securing said light sources and said light detector means in optical contact with said subject.

4. The apparatus of claim 1 wherein said probe further comprises:

light detector means for producing signals indicative of a light intensity of said at least two beams of light received from said tissue of a subject.

5. The apparatus of claim 4 wherein said probe further comprises:

at least two electrical conductors interconnected at a first end thereof to said light detector means and connectable by said first and second connector segments at a second end thereof to mating ones of said plurality of electrical conductors in said interconnector cable to interconnect said light detector means with said measurement system.

6. The apparatus of claim 5 wherein said second end of said at least two electrical conductors are interconnected with said plurality of electrical conductors by a pin and socket connector system located in said first and second connector segments.

7. The apparatus of claim 1 wherein said interconnector cable further comprises:

means for latching said first and second connector segments.

8. The apparatus of claim 7 wherein said latching means includes an opening of predetermined geometric shape in said first connector segment to receive a tab element included in said second connector segment when said first connector segment is interconnected with said second connector segment.

9. The apparatus of claim 8 wherein said latching means further comprises a user activated spring to release said tab element from said opening when said first connector segment is interconnected with said second connector segment.

10. The apparatus of claim 1 wherein said attachment means comprises:

a first housing section;

a second housing section hingeably attached to said first housing section to form a clamshell-type housing, said first and said second sections being rotatable between an open and a closed position and having an aperture in one end thereof when in said closed position to receive a member of a patient, with said first and said second housing sections both having an interior surface facing each other and an exterior surface.

11. The apparatus of claim 10 wherein said first housing section includes:

notch means for securing said plurality of conductors to said first housing section.

12. The apparatus of claim 10 wherein said second housing section includes a depression in said interior surface of said second housing section and of topology to substantially match the contours of said member.

13. The apparatus of claim 10 wherein said releasably attaching means further comprises:

spring means for biasing said first and said second housing sections in their closed position.

14. The apparatus of claim 10 wherein said attachment means further comprises:

adhesive sheet means attached to said interior surface of said second housing section for attaching said second housing section to said member when said first and said second sections are in said closed position to place said adhesive sheet means in contact with said member positioned between said first and said second housing sections.

15. The apparatus of claim 14 wherein said attachment means further comprises:

deformable means attached to said interior surface of said first housing section for compliantly conforming to said member when said first and said second housing members are in said closed position to place said deformable means in contact with said member.

16. Apparatus for illuminating tissue of a subject to measure light absorption of said tissue by a measurement system, comprising:

a first connector segment having an opening on one side thereof;

at least two laser diode light sources, mounted in said first connector segment, for generating at least two beams of light of different wavelengths for application to said tissue through said opening;

a plurality of electrical conductors electrically interconnected between said at least two laser diode light sources and said measurement system;

at least two electrical connector contacts mounted in said first connector segment and connected to a like number of said plurality of electrical conductors;

a second connector segment, removably interconnectable with said first connector segment, having at least two electrical connector contacts for mating with said at least two electrical connector contacts mounted in said first connector segment when said first and second connector segments are interconnected;

means, attached to said second connector segment, adapted for removably attaching said second connector segment to said subject;

means for applying said at least two beams of light to said tissue wherein said applying means comprises an optical port located in said second connector segment substantially adjacent said opening in said first connector segment when said first connector segment is removably interconnected with said first connector segment; and light detector means, connected to said at least two electrical connector contacts in said interior surface of said second connector segment, for producing signals indicative of a light intensity of said at least two beams of light received from said tissue of a subject.

17. The apparatus of claim 16 wherein said removably attaching means comprises:

a flexible support structure for securing said light sources and said light detector means in optical contact with said subject.

18. The apparatus of claim 16 wherein said applying means comprises;

an optically transmissive window disposed in said second connector segment wherein said generated beams of light from said first connector segment are optically transmitted through said window in said second connector segment to impinge on said tissue, when said first and second connector segments are removably interconnected.

19. The apparatus of claim 16 wherein said removably attaching means comprises:

a first housing section;

a second housing section hingeably attached to said first housing section to form a clamshell-type housing, said first and said second sections being rotatable between an open and a closed position and having an aperture in one end thereof when in said closed position to receive a member of a patient, with said first and said second housing sections both having an interior surface facing each other and an exterior surface.

20. The apparatus of claim 19 wherein said removably attaching means further comprises:

adhesive sheet means attached to said interior surface of said second housing section for attaching said second housing section to said member when said first and said second sections are in said closed position to place said adhesive sheet means in contact with said member positioned between said first and said second housing sections.

21. The apparatus of claim 20 wherein said removably attaching means further comprises:

deformable means attached to said interior surface of said first housing section for compliantly conforming to said member when said first and said second housing members are in said closed position to place said deformable means in contact with said member.

22. The apparatus of claim 16 wherein said interconnection means further comprises:

means for latching said first and second connector segments.

23. The apparatus of claim 22 wherein said latching means includes an opening of predetermined geometric shape in said first connector segment to receive a tab element included in said second connector segment when said first connector segment is interconnected with said second connector segment.

24. The apparatus of claim 23 wherein said latching means further comprises a user activated spring to release said tab element from said opening when said first connector segment is interconnected with said second connector segment.

25. The apparatus of claim 24 wherein said first housing section includes:

notch means for securing said plurality of conductors to said first housing section.

26. The apparatus of claim 24 wherein said second housing section includes a depression in said interior surface of said second housing section and of topology to substantially match the contours of said member.

27. The apparatus of claim 24 wherein said releasably attaching means further comprises:

spring means for biasing said first and said second housing sections in their closed position.

* * * * *